(12) United States Patent
Grier et al.

(10) Patent No.: US 7,390,461 B2
(45) Date of Patent: Jun. 24, 2008

(54) BROAD SPECTRUM OPTICALLY ADDRESSED SENSOR

(75) Inventors: David G. Grier, Chicago, IL (US);
Lewis Gruber, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 741 days.

(21) Appl. No.: 10/428,785

(22) Filed: May 5, 2003

(65) Prior Publication Data
US 2004/0058455 A1    Mar. 25, 2004

(51) Int. Cl.
*G01N 21/00* (2006.01)
*G01N 33/545* (2006.01)
*B32B 5/16* (2006.01)
*A61B 17/20* (2006.01)
*B01J 19/08* (2006.01)
*G02B 5/02* (2006.01)

(52) U.S. Cl. ............... 422/82.05; 252/582; 422/186; 428/403; 436/531; 604/22

(58) Field of Classification Search .......... 422/82.05, 422/186; 252/582; 428/403; 436/531; 604/22
See application file for complete search history.

(56) References Cited

U.S. PATENT DOCUMENTS

| | | | |
|---|---|---|---|
| 4,627,689 A | 12/1986 | Asher | |
| 4,632,517 A | 12/1986 | Asher | |
| 5,854,078 A | 12/1998 | Asher et al. | |
| 5,898,004 A | 4/1999 | Asher et al. | |
| 6,022,748 A | 2/2000 | Charych et al. | |
| 6,055,106 A | 4/2000 | Grier et al. | |
| 6,187,599 B1 | 2/2001 | Asher et al. | |
| 6,224,566 B1* | 5/2001 | Loeb | 604/22 |
| 6,331,438 B1 | 12/2001 | Aylott et al. | |
| 6,544,800 B2* | 4/2003 | Asher | 436/531 |
| 6,737,634 B2* | 5/2004 | Curtis et al. | 250/222.2 |

FOREIGN PATENT DOCUMENTS

| | | | |
|---|---|---|---|
| WO | 00/73777 A1 | | 12/2000 |
| WO | WO 0106244 | * | 1/2001 |
| WO | WO01/01141 A1 | * | 4/2001 |

OTHER PUBLICATIONS

International Search Report for PCT/US03/13972.

(Continued)

*Primary Examiner*—Jili Warden
*Assistant Examiner*—Lore Ramillano
(74) *Attorney, Agent, or Firm*—Evan Law Group LLC (57) ABSTRACT

The present invention relates to a sensor for detecting chemical, biological, biochemical or other environmental stimuli, and includes a plurality of colloidal particles having chemical receptors bound to each particle's surface, wherein when a target stimulus is directed to the bound chemical receptor, the gelled matrix contracts or expands, which changes the lattice constant, thereby changing the pattern of diffracted light in a measurable manner so that the target stimulus' presence can be detected by a spectrometer. The plurality of colloidal particles are composed of a material having a first dielectric constant, and the gel and surrounding medium have a second dielectric constant. The colloidal particles can be assembled using holographic optical tweezers and polymerized to create an integrated sensor array, which diffracts light in a detectable characteristic manner.

71 Claims, 9 Drawing Sheets

OTHER PUBLICATIONS

International Preliminary Examination Report for PCT/US03/13972.

European Search report dated Jun. 1, 2006 for corresponding application No. PCT/US0313972.

Seitz, W. R., et al., "Derivatized, swellable polymer microspheres for chemical transduction"., Analytica Chemica Acta, vol. 400, pp. 55-64, (1999).

Wang, H., et al., "pH Sensor based on swellable poly(3-nitro-4-hydroxystyrene) microspheres in a hydogel"., Part of the SPIE Conference on Internal Standardization and Calibration Architectures for Chemical Sensors. Boston Massachusetts, vol. 3856, pp. 224-231, Sep. 1999.

"Optical Gel Senses Chemicals". Optical Gel Senses Chemicals, Jan. 1998.

"Contact Lens Could Measure Glucose For Diabetes". Pittsburgh Business Times, Apr. 14, 2003, American City Business Journals, Inc., 2003.

\* cited by examiner

BROAD SPECTRUM OPTICALLY ADDRESSED SENSOR

The present invention relates to a broad spectrum sensor and a method of manufacturing the sensor, the sensor which detects chemical, biological, biochemical, or other environmental stimuli based on their influence on the mechano-optical properties of the sensor material.

BACKGROUND OF THE INVENTION

Chemical sensors may be based on crystalline domains of colloidal particles embedded in a gelled matrix. Appropriately prepared gels, such as hydrogels, can swell and contract in response to changes in their physical or chemical environment. The embedded colloidal crystal's lattice constant changes as the gel swells, and its optical diffraction properties vary accordingly, in a manner that may be detected. This response can be optimized for a particular stimulus by introducing functional groups, into the gel capable of interacting with the stimulus and inducing the desired structural changes to the gel.

Implementations of this technique have incorporated the necessary functional groups directly into the polymer from which the gel is constituted (see Asher, U.S. Pat. No. 6,544,800, and Asher et al., U.S. Pat. Nos. 5,187,599, 5,854,078, and 5,898,004—hereafter the "Asher patents"). Once a gel is functionalized in this way, it swells preferentially in response to the specific stimulus, and the embedded colloidal particles are used as passive tracers of the mechanical state or degree of swelling of the functionalized hydrogels. As described in the Asher patents, the gels' swelling is monitored by measuring the optical properties of a colloidal crystal embedded within the gel. Variations in lattice constant change the diffraction pattern of the colloidal crystal in a way which can be measured.

In particular, as described in the Asher patents, uniformly sized colloidal spheres were allowed to organize themselves into a self-assembled crystal, and then the hydrogel, incorporating a concentration of selected functional groups, was polymerized around the as-formed crystal. Once formed, the functionalized gelled crystal can be used as quantitative sensors for the stimulus to which the functional groups respond by monitoring their diffraction using an optical spectrometer. Incorporating different functional groups into different gels results in a variety of sensor materials sensitive to various specific environmental stimuli, each gel sensitive to a specific stimulus.

However, the above approach by the Asher patents are only effective for detecting one stimulus at a time, and they cannot be scaled up easily to monitor a spectrum of potential stimuli. Further, combining several sensor crystals into a single system capable of detecting and distinguishing different stimuli poses significant practical difficulties, would require post-synthesis assembly, which is a difficult process. Further, no method exists for synthesizing distinctly functionalized regions of gel in close proximity.

Still further, allowing colloidal spheres to self-assemble into a colloidal crystal and then creating a gel around the resulting lattice as described in the Asher patents, introduces undesirable variability into the optical properties of the resulting sensor, both because a self-assembled colloidal crystal suffers from structural defects, and also because very little control is possible over the crystal lattice constant, and still less over its symmetry.

Finally, if the individual self-assembled crystal had indistinguishable or unpredictable optical properties, then detecting the different responses to different stimuli in a sensor array would require position-sensitive detection, which is costly. Having sensor domains with distinctive optical signatures would be less costly and difficult, but achieving such control during colloidal crystallization is extremely difficult, and may be impossible.

Thus, a broad spectrum sensor that can detect and monitor large numbers of disparate environmental stimuli simultaneously, and that is easy and inexpensive to manufacture, is needed.

SUMMARY OF THE INVENTION

The present invention relates to a sensor for detecting chemical, biological, biochemical or other environmental stimuli, including a plurality of colloidal particles having chemical receptors bound to each particle's surface, wherein the plurality of colloidal particles are composed of a material having a first dielectric constant, and wherein the particles are formed into a one-, two- or three-dimensional lattice.

The lattice is surrounded by a gelled matrix which is capable of expanding or contracting depending upon changes in the particular local environment and which has a second dielectric constant.

When a target stimulus is directed to the sensor, and more specifically, to the bound chemical receptor, the gelled matrix contracts or expands, which changes the lattice constant, thereby changing the pattern of diffracted light in a measurable manner so that the target stimulus' presence can be detected by a spectrometer.

In another embodiment consistent with the present invention, the plurality of colloidal particles are assembled using holographic optical tweezers and polymerized to create an integrated sensor array, which diffracts light in a characteristic manner, with each one-, two- or three-dimensional crystalline domain of particles and each two-dimensional crystalline domain of particles diffracting a distinct color by design into a particular direction.

In another embodiment consistent with the present invention, monolayer and thin three-dimensional sensors permit easier access of target stimuli and improve the sensitivity of the gelled sensor crystal domain.

In yet another embodiment consistent with the present invention, distinct sensor domains can be stacked on top of one another in three dimensions to monitor and correct for drifts in the sensor domains' lattice constants due to environmental factors, and can be used to distinguish between closely related stimuli. Non-functionalized and differentially functionalized domains in one-, two- or three-dimensional arrangements also can be used to achieve the same result.

In yet another embodiment consistent with the present invention, two- or multiple-stage detection techniques in which the sensor is first exposed to possible stimuli and subsequently processed to detect the stimuli can be used to achieve the same result.

In yet another embodiment consistent with the present invention, the gelled sensor arrays can be placed at the end of optical fibers for optical readout with a fiber spectrometer, and integrated into portable systems for use in detecting chemical, biological, biochemical or other environmental stimuli.

In yet another embodiment consistent with the present invention, gelled sensors can be provided in a bundle or "brush" and an operator may examine a large area by sweeping the sensor bundle or brush over the targeted area. The brush arrangement provides contact of the sensing element with targets in situ as opposed to having to transfer a sample to a chip.

In yet another embodiment consistent with the present invention, instead of gelled sensor arrays, beads which are responsive to a particular target stimulus, can be disposed, and can be arrayed, at the end of each fiber of the brush to provide the response to the target stimulus.

In yet another embodiment consistent with the present invention, a sleeve can be provided around the brush to provide a sufficiently rigid structure to insert the sensors into a loosely packed material, for example. Further, a hardened permeable screen can be provided on the tip of each fiber of the brush such that the gel of the sensor array is not abraded during use.

In another embodiment consistent with the present invention, a target stimulus can be introduced to the gelled sensor array that interacts with functional groups on the spheres' surfaces so as to bind the specifically functionalized spheres together. After this, the gel can be swelled non-specifically through a change in temperature of chemical environment. Spheres bound together by the action of the stimulus will not separate in response to the swelling, and thus, the diffractive properties of their crystalline domain will not change. By contrast, differently functionalized spheres not acted upon by the stimulus will separate as the gel swells, and their diffractive properties will change. In this case, detection of the target stimulus involves the absence of color change upon swelling. This approach would be useful, for example, in the specific detection of antigens through their ability to bind spheres functionalized with the associated antibodies.

There has thus been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DETAILED DESCRIPTION OF THE INVENTION

The present invention relates to a colloidal crystal sensor and a method of manufacturing the colloidal crystal sensor, which includes (1) functionalizing the colloidal particles themselves, rather than the embedding gel, and (2) using holographic optical trapping techniques to assemble one or more types of functionalized colloidal particles into precisely structured domains with specified chemical and optical properties.

In particular, the colloidal crystal sensor can be functionalized to perform chemical, biological, and physical sensing by appending functional chemical groups to the surfaces of colloidal particles, the groups which are designed to respond to a selected stimulus by modifying the local chemical environment within the gel, for example, by changing the local ionic strength, temperature, chemical composition, or changing the pH. The gel either shrinks or swells in response, thereby altering the separation between the colloidal particles or spheres in the colloidal crystal. The functionalized crystal's changing lattice constant, and thus, its diffraction characteristics, can be measured with a spectrometer so that the target stimulus+ presence can be detected. The target stimulus can be one of a nucleic acid, protein, carbohydrate, and lipid.

Figure 1:
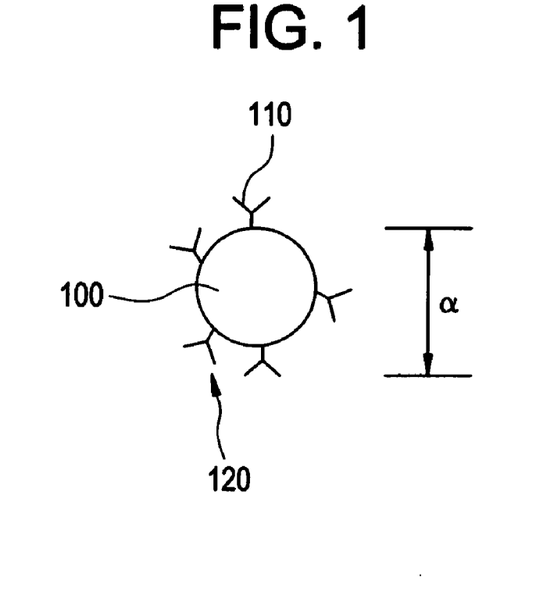
FIG. 1 is a schematic representation of a functionalized colloidal particle according to one embodiment consistent with the present invention.

FIG. 1 schematically depicts a functionalized colloidal particle 120, indicated as, for example, a colloidal sphere 100, with a specific type of chemical receptor 110 bound to its surface. The colloidal particle 100 itself can be fabricated from silica, polystyrene, titanium oxide, or any other material which has the appropriate or desired optical properties, and does not react specifically or non-specifically with any of the predetermined target environmental stimuli.

The ligand or chemical receptor 110 should be selected to respond specifically to a chosen stimulus, for example by chemically binding a target molecule or by catalyzing a chemical reaction when acted upon by the stimulus. This ligand 110 should be irreversibly bound to a surface of the particle or sphere 100. Different populations of particles or spheres 120 may be created by appending different ligands 110 to their surfaces. These populations also may be distinguished by the size, shape, and material composition of their particles. In the case of spherical particles, the size may be described by the diameter "a" (see FIG. 1).

Figure 2:
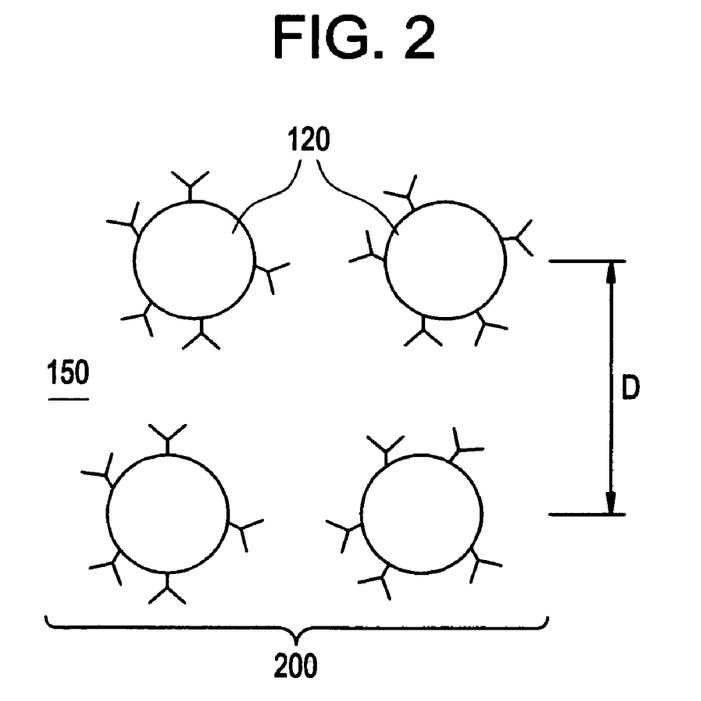
FIG. 2 is a schematic representation of a unit cell of a colloidal crystal composed of functionalized colloidal particles according to one embodiment consistent with the present invention.

FIG. 2 schematically depicts a unit cell 200 of a colloidal crystal composed of functionalized particles 120, shown as spheres 102, from a single population organized into a periodic lattice 200 with a characteristic spacing "D". The lattice 200 is represented as a single unit cell 200 of a simple two-dimensional square array, but one of ordinary skill in the art would know that the lattice may take any form from the general class of crystalline structures either in one layer, or else in multiple layers.

For this lattice or array 200 to function as a diffractive optical element, the particles or spheres 100 should be made of a material whose dielectric constant differs from that of the surrounding medium 150. Under these conditions, light passing through the medium 150 is scattered by the particles or spheres 100, and the coordinated scattering from the regularly positioned particles or spheres 100 results in the desired diffraction. In particular, light of wavelength λ impinging on such an arrangement of particles or spheres 100 is diffracted by lines (in two dimensions) or planes (in three) of particles or spheres 100 by an angle θ that is given by Bragg's law:

$$\sin \theta = n\lambda/D$$

where n is a whole number, n=0, 1, 2, . . .

Conversely, the wavelength of light scattered into a given direction θ is given by:

$$\lambda = D \sin \theta / n$$

The size and shape of the particles or spheres 100 may influence the observed diffraction pattern, and dynamic diffraction theory generally will be required to predict the diffraction pattern for a particular wavelength of light. Even so, the wavelength scattered into a given direction will depend on the lattice constant.

Figure 3:
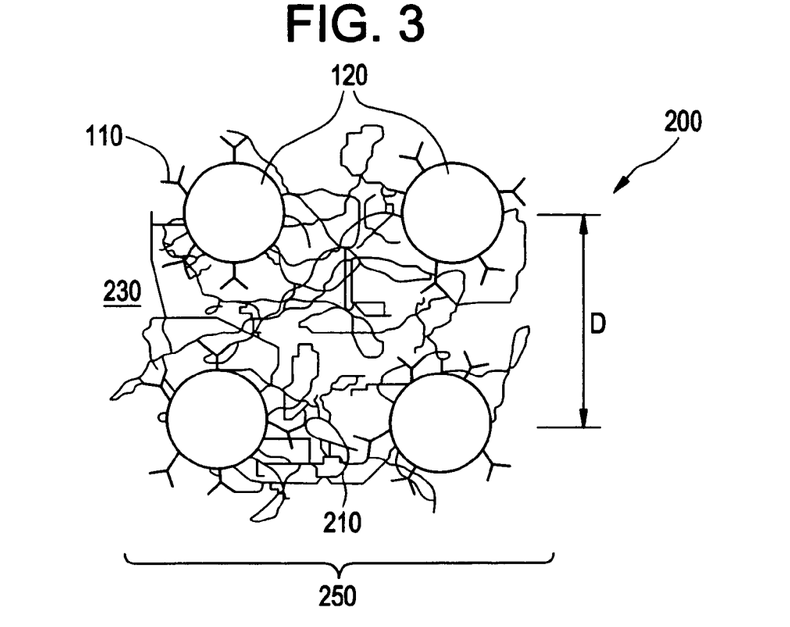
FIG. 3 is a schematic representation of a gelled sensor crystal according to one embodiment consistent with the present invention.

FIG. 3 shows a gelled crystal sensor 250, with the lattice 200 of functionalized particles or spheres 120 embedded in a gelled matrix 210. The gel 210 may come from the class of hydrogels, in which case the fluid medium 230 supporting both the spheres 120 and the gel 210 would be water. Other gels and solvents might be used as desirable for particular applications, as one of ordinary skill in the art would recognize. The gel 210 can be formed around an already assembled colloidal crystal 250 by, for example, photopolymerization, chemically-induced polymerization, thermally-induced polymerization, or by other means known to one of ordinary skill in the art.

The gel 210 should be formulated so that its specific volume increases or decreases (i.e., swells or shrinks) in response to changes in its local environment, thereby altering the separation D between the spheres in the colloidal crystal 250. Relevant changes may include changes in salt concentration, local ionic strength, changes in pH, or changes in concentrations of chemical species in the solution. Preferably, the gel 210 should not respond strongly by itself to any of the target stimuli for which the sensor array 200 is designed. Rather, the target stimuli should interact with the ligands 110 bound to the particles or spheres 100 to effect a chemical change to which the gel 210 will respond. The colloidal particles or spheres 100, ligands 110, gel 210, and solvent 230 should be selected accordingly. As an example, crown ethers chemically bonded to the surfaces of the particles or spheres 120 specifically bind lead ions in aqueous solutions, thereby raising the local ionic strength and shrinking the surrounding hydrogel.

As the gel 210 shrinks or swells, so does the lattice constant of the embedded colloidal crystal 200. This in turn influences the colloidal crystal's 200 diffraction characteristics. The functionalized crystal's 200 changing lattice constant therefore, can be monitored by illuminating it with white light and measuring the wavelength of backscattered light. Quite precise measurements are possible with commercially available hand-held fiber optic spectrophotometers.

Figure 4A:
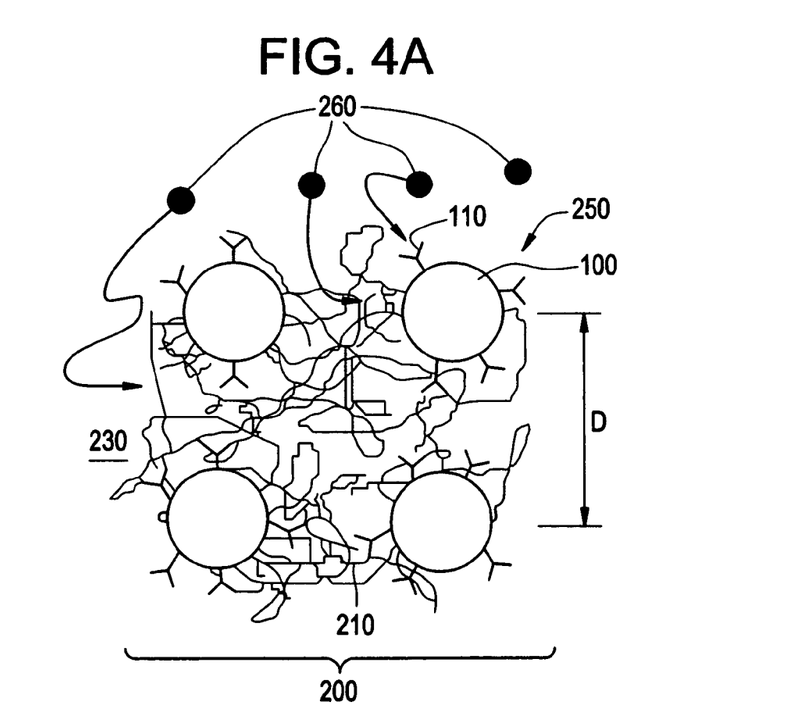
FIG. 4A is a schematic representation of a principle of stimulus detection by a gelled crystal domain, where the target stimulus is introduced into the gel, according to one embodiment consistent with the present invention.
Figure 4B:
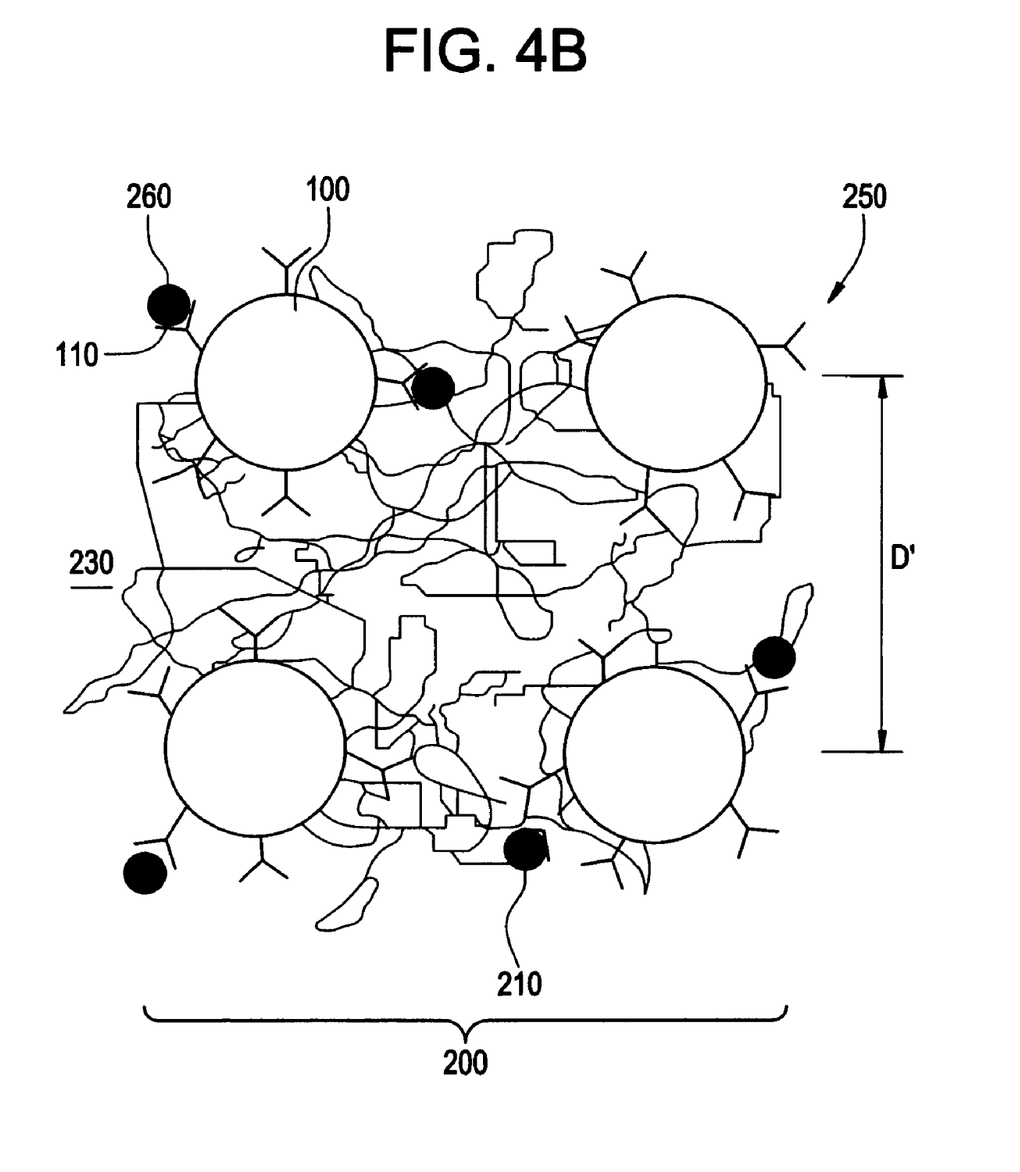
FIG. 4B is a schematic representation of a principle of stimulus detection by a gelled crystal domain, where the individual target stimulus molecules bind to ligands affixed to the individual particles, according to one embodiment consistent with the present invention.

FIGS. 4A and 4B show a gelled crystal sensor 250 detecting its designed target stimulus, depicted schematically as small spheres 100. Individual stimulus molecules 260 (see FIG. 4A) bind to ligands 110 affixed to individual particles or spheres 100 (see FIG. 4B). This interaction leads by design to chemical changes at the particle's or sphere's 100 surface which propagate into the surrounding gel 210. By design, these chemical changes cause the gelled crystal 200 to swell, changing the lattice constant of the embedded colloidal crystal 200 to change from D to D'. This in turn changes the wavelength of light scattered into a particular direction, so that the presence of the target stimulus' 260 can be detected.

Thus, the functional ligands 110 are affixed to the colloidal particles 100 rather than to the surrounding gel 210. This offers an advantage in that libraries of different particles 100 can be formed into different types of sensors 250 using the same gel chemistry. Moreover, it also offers a means to create multiple self-calibrating sensors on a single device.

By functionalizing the particles or spheres 100 rather than the gel 210, multiple detectors can be integrated into a single piece of gel 210, thereby creating a highly compact and comparatively inexpensive sensor 250.

For a given choice of gel 210 or solvent, the class of distinct particles 100 and ligands 110 which satisfy these design criteria define the range of target stimuli 260 which may be individually and simultaneously detected with a single gelled crystal sensor 250.

Figure 5:
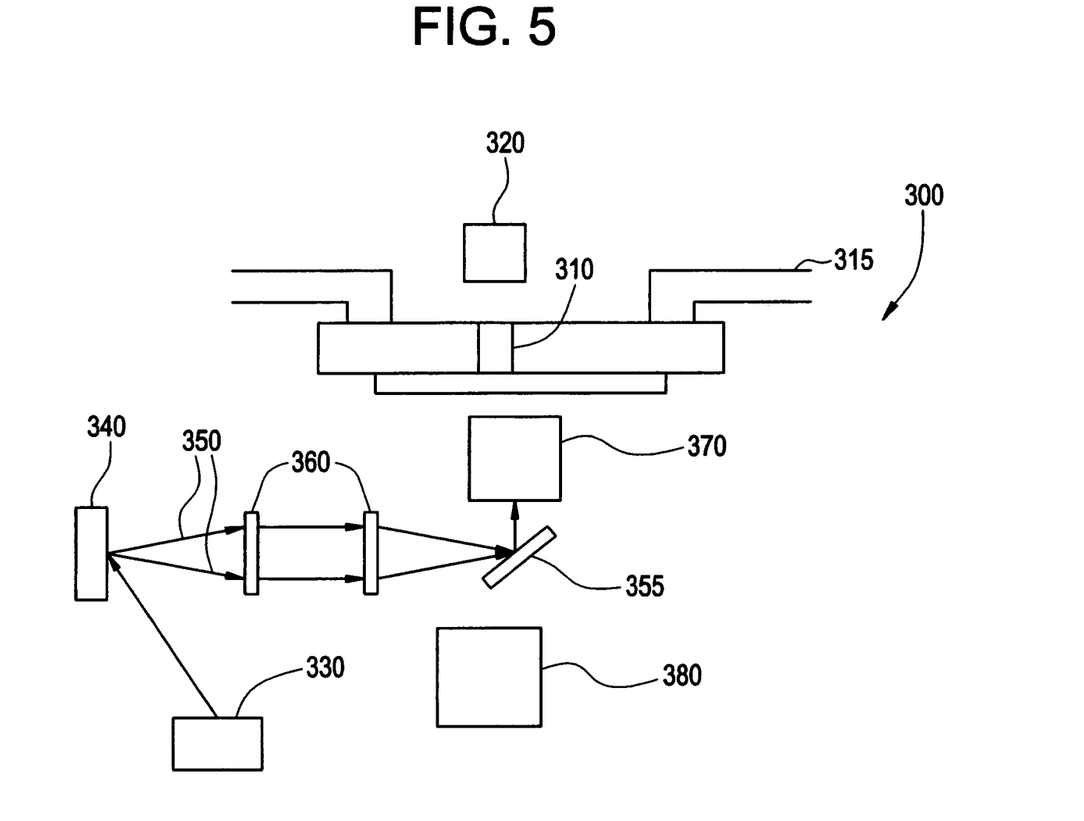
FIG. 5 is a schematic representation of a holographic optical tweezer system, according to one embodiment consistent with the present invention.

In another embodiment consistent with the present invention, instead of requiring colloidal particles to self-assemble into crystalline domains, assembly of the colloidal particles can be performed using holographic optical tweezers 300 (see FIG. 5).

In conventional sensors, allowing colloidal particles to self-assemble into a colloidal crystal and then creating a gel around the resulting lattice introduces variability into the optical properties of the resulting sensor, both because self-assembled colloidal crystals may suffer from structural defects, and also because it may be difficult to control the resulting crystal's lattice constant, and its symmetry.

However, by using holographic optical tweezers 300 (see FIG. 5), particles can be selected or trapped from a reservoir of particles, and moved to an assembly area, and organized into any desired configuration, including three-dimensional array configurations, quickly, cheaply, and effectively. The configuration need not be related to any structure which the colloidal particles naturally would form by self-assembly; nor does the lattice spacing of the tweezer-formed crystal have to be related to the natural balance of forces between the particles. Consequently, the particles can be optimized for their optical and chemical characteristics without concern for their mutual interactions. For this reason, the colloidal particles used for this purpose need not be spherical, nor necessarily of precisely specified sizes.

Holographic optical tweezers 300 are known in the art, and are described in U.S. Pat. No. 6,055,106 to Grier et al., which is herein incorporated by reference. As used in the present invention, and as shown for example, in FIG. 5, the holographic optical tweezers 300 organize, for example, 200 colloidal particles within a transparent and chemically inert flow chamber 315, into a three-dimensional array. A sample volume 310 within the chamber 315 is illuminated by an illuminator 320. Optical traps are crafted from a single input laser beam 330 reshaped by a computer-addressed diffractive optical element (i.e., spatial light modulator 340) into a fan-out of diffracted beams 350 which are passed through a series of lenses 360, each of the diffracted beams 350 which is directed by a dichroic mirror 355 and focused by high-power objective lens 370 into an optical trap. Each colloidal particle in the pattern organized by the holographic optical tweezers 300, is held in place by a precisely positioned optical trap.

Light from the resulting optical tweezers 300 is viewed by a video camera 380 together with a microscope image of the resulting array of colloidal particles (polystyrene spheres in this case), dispersed in water and organized into a square array by the traps.

Regular arrays of colloidal particles are known as colloidal crystals and have extraordinary diffraction properties for visible light. They may be thought of as three-dimensional diffraction gratings whose characteristic diffraction patterns depend on the crystals' symmetry and lattice constant. The crystals' distinctive optical properties are optimized by fabricating precisely structured colloidal arrays, and they are exploited here as part of a method of measuring concentrations, doses, and fluxes of environmental stimuli.

Figure 6:
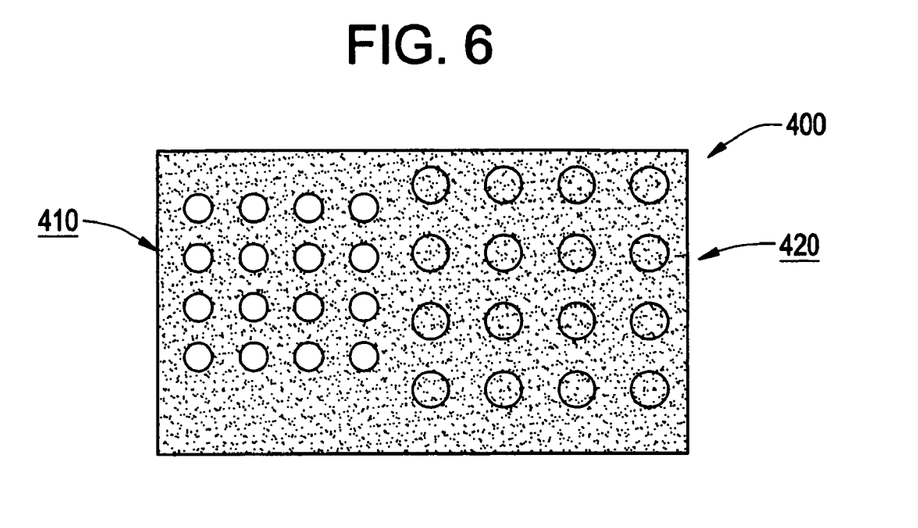
FIG. 6 is a schematic representation of distinct functionalized domains arranged into an integrated sensor array, according to one embodiment consistent with the present invention.

In another embodiment consistent with the present invention, as shown in FIG. 6, different colloidal particles from different libraries can be organized simultaneously in this manner to form separate domains distinguished both by their chemical functionalization and by their optical characteristics. These separate domains can be placed into arbitrarily close proximity and even rearranged relative to each other using the capabilities of the dynamic holographic optical tweezers 300 of FIG. 5. Once the desired arrangement of colloidal particles or spheres within domains, and domains within the region, is attained, the entire assembly can be polymerized to create an integrated sensor array 400 as shown in FIG. 6.

FIG. 6 shows two domains 410, 420 composed of functionalized colloidal particles or spheres 120 differing in their surface ligands and in their crystal lattice structure arranged side-by-side in the same gel matrix to form a sensor array 400.

Even if only one or two target stimuli are of interest, the present heterogeneous sensor array offers advantages over competing technologies. In particular, multiple distinct domains offer continuous in situ calibration, redundant cross-correlated detection, and superior discrimination of closely related target stimuli.

In another embodiment consistent with the present invention, sensor arrays are composed of distinct one-dimensional chains of particles or distinct two-dimensional domains of particles in a monolayer, and will still diffract light in a characteristic manner, with each chain and each domain diffracting a distinct color by design into a particular direction.

Figure 7A:
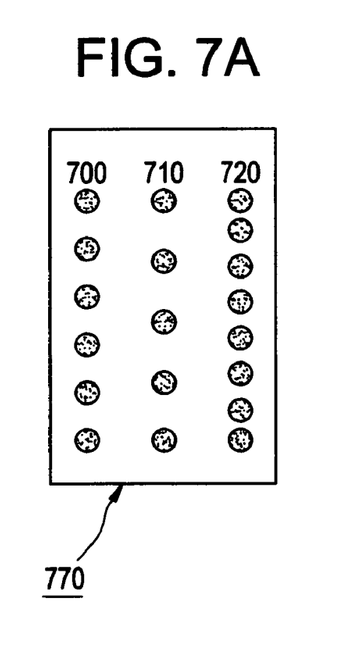
FIGS. 7A and 7B are schematic representations of sensor array composed of distinct one-dimensional chains of particles and distinct two-dimensional domains of particles in a monolayer, according to one embodiment consistent with the present invention.

In this respect, FIG. 7A depicts three one-dimensional crystals of functionalized colloidal spheres, 700, 710, and 720, arranged into a sensor configuration 770 using holographic optical tweezers. Each line of spheres 700, 710, 720 has a distinct spacing, and thus, a distinguishable diffraction signature.

Figure 7B:
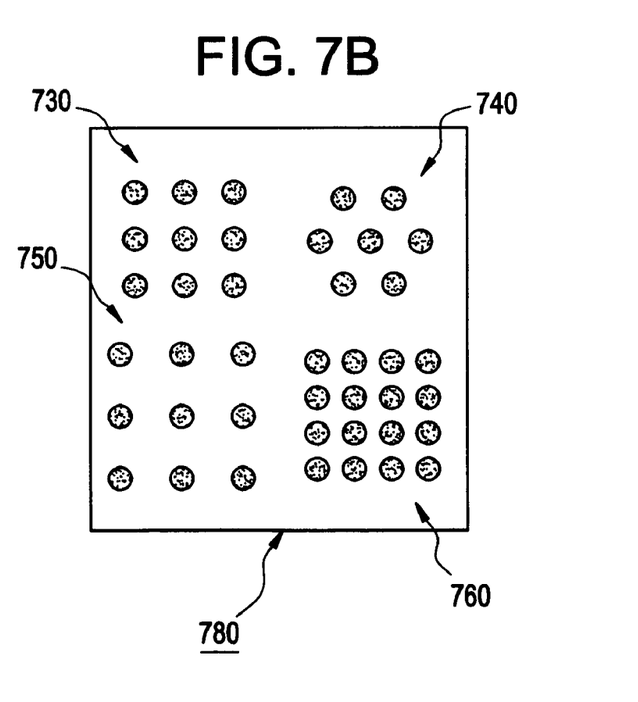

Further, FIG. 7B depicts four two-dimensional functionalized colloidal crystals 730, 740, 750 and 760, arranged into a sensor configuration 780 using holographic optical tweezers. Each domain has a characteristic spacing, as in 730, 750, and 760, or a characteristic spacing and symmetry, as in 740.

Figure 8:
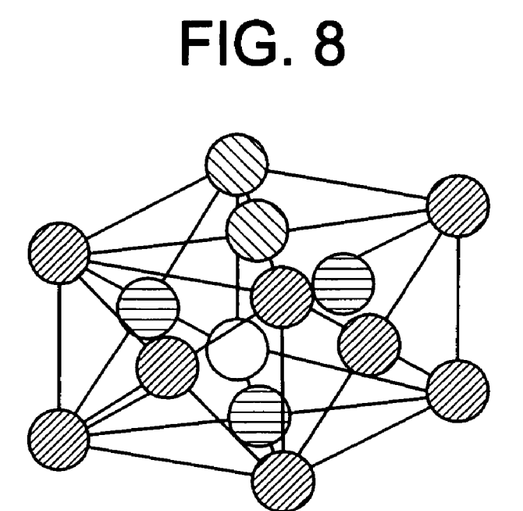
FIG. 8 is a schematic representation of a three-dimensional domain of particles according to one embodiment consistent with the present invention.

Three-dimensional domains as shown in FIG. 8, will scatter light more strongly than either lower-dimensional structure, and offer the possibility of strong back-scattering (i.e., scattering by 180 degrees). Strong backscattering may be desirable for some optical detection schemes and can be emphasized by increasing the mismatch in dielectric constant between the colloidal particles and the surrounding fluid and gel. High dielectric constant materials such as titanium dioxide may be preferred for the particles in such circumstances. The use of such high dielectric constant particles will greatly diminish the penetration depth of light at the diffracted wavelength into the crystal, so that two or three layers may suffice to achieve essentially complete backscattering.

Monolayer and thin three-dimensional sensors have advantages over thick sensors in that they permit easier access of target stimuli into their interiors and thus, can exhibit a strong response with comparatively few target molecules. This improves the sensitivity of the gelled sensor crystal domain.

In this regard, FIG. 8 depicts one unit cell of a three-dimensional face-centered cubic lattice of colloidal spheres. Such a three-dimensional crystalline configuration has a distinctive diffraction pattern whose peaks depend on the spacing between particles. Different crystalline symmetries and lattice spacings lead to different distinguishable diffraction patterns.

Following this approach, as stated above, several different domains sensitive to several different stimuli can be incorporated into a single sensor material (see FIG. 6). This material then can be observed with a spectrophotometer, such as a hand-held fiber spectrophotometer sold by Ocean Optics, for example. Each domain's diffraction pattern will be clearly resolved as one or more distinct diffraction peaks registered by the spectrophotometer. Introducing a stimulus for one of the domains will cause its characteristic diffraction peak to shift wavelength. This shift in wavelength can be resolved by the spectrophotometer and used to report the presence of that specific stimulus, and its concentration. The use of a gelled sensor array integrated into an optical detection system is further described below with respect to FIG. 12.

Figure 9:
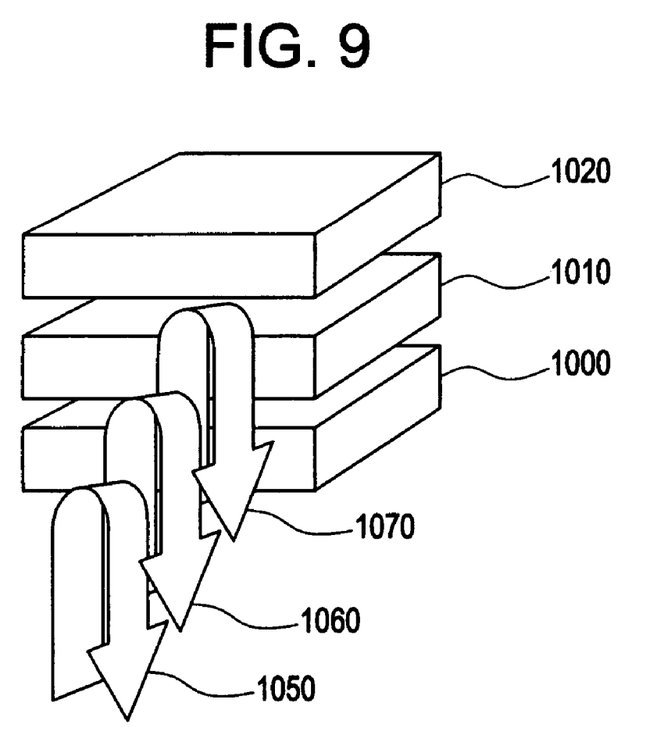
FIG. 9 is a schematic representation of a single sensor material incorporating several different domains stacked on top of each other in three dimensions, and sensitive to several different stimuli, according to one embodiment consistent with the present invention.

In another embodiment consistent with the present invention, distinct sensor domains also can be stacked on top of each other in three dimensions provided that the domains' optical properties are designed to permit illuminating light to pass through to all of the domains and diffracted light to pass through to the detector (see FIG. 9).

As shown in FIG. 9, three optically distinct colloidal crystalline domains are stacked in three dimensions. (Note that there is no actual space between the domains, but the drawings depict a space for understanding of the invention only). In particular, domain 1000 is designed to reflect the wavelength of beam 1050, but to transmit the wavelengths of beams 1060 and 1070. Similarly, domain 1010 reflects the wavelength of beam 1060, and transmits the wavelength of beam 1070. Finally, the wavelength of beam 1070 is reflected by domain 1020. Thus, if the lattice constant of any one of the domains 1000, 1010 or 1020 were to change, the resulting change in diffraction pattern would be clearly visible, even through the other two domains.

Stacking detecting domains in this manner might appear to offset the benefits of improved sensitivity and response time offered by thin sensors. In some applications, however, the resulting systems' stacking may offer additional advantages.

Figure 10A:
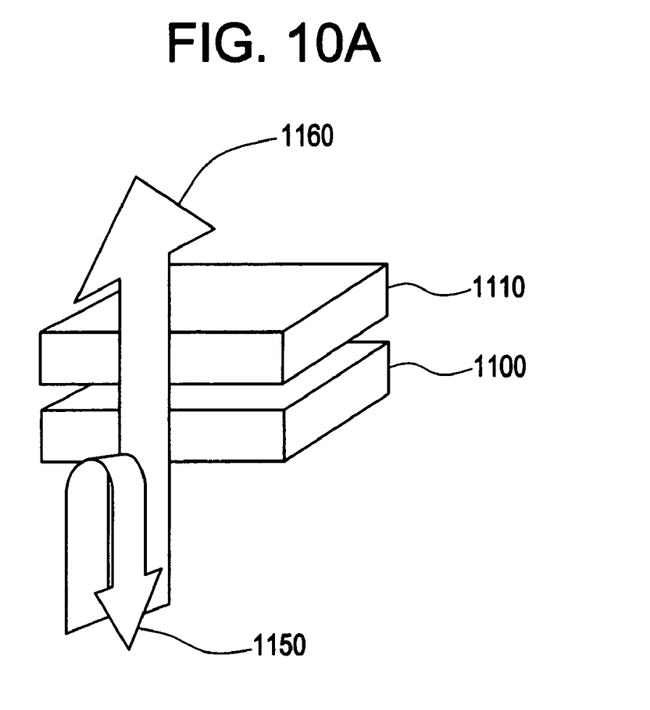
FIG. 10A is a schematic representation of a sensor domain composed of functionalized particles stacked atop an otherwise identical domain of particles whose surfaces are not functionalized, according to one embodiment consistent with the present invention.

For example, consider a sensor domain composed of functionalized particles stacked atop an otherwise identical domain of particles whose surfaces are not functionalized (see FIG. 10A). As shown in FIG. 10A, two gelled colloidal crystalline domains 1100 and 1110, are both designed to reflect the wavelength of beam 1150, but to transmit other wavelengths such as that of beam 1160. The only difference is that domain 1110 is functionalized to swell in response to stimulus 1190, while domain 1100 is not. Thus, in the absence of a stimulus, the two layer domains would diffract light as one. Once the stimulus arrives, however, the upper functionalized domain would respond while the lower non-functionalized domain would not.

Further, one-dimensional chains of non-functionalized particles could be used in between functionalized domains to monitor inter-domain cross-talk.

Figure 10B:
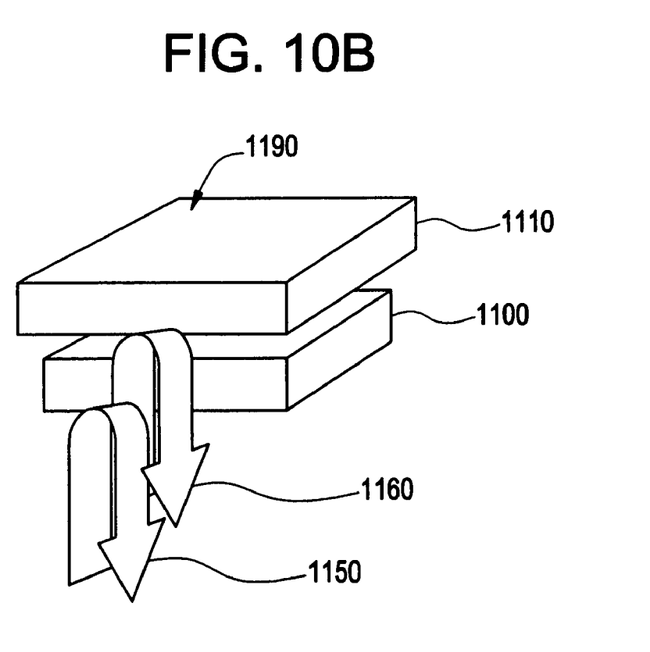
FIG. 10B is a schematic representation of the stacked particles of FIG. 10A, showing the response of the upper functionalized domain in comparison to the lower non-functionalized domain, according to one embodiment consistent with the present invention.

FIG. 10B shows the response to stimulus 1190. The functionalized domain 1110 swells in response to the stimulus. As a result, the lattice constant of 1110 changes so that the wavelength of beam 1160 no longer is transmitted, but rather, is reflected. This reflected light will pass through domain 1100 whose lattice is not functionalized, and therefore, whose diffraction pattern will change little if at all to the stimulus 1190. Any passively induced change in the lattice constants of domains 1100 and 1110 will be evident in common mode shifts of the diffracted wavelengths of beams 1150 and 1160. The concentration of the stimulus will be evident in the differential shifts of the diffraction peaks.

Thus, in the case shown in FIG. 10B, the response to the stimulus will be measured when the single diffraction peak either broadens by a measurable amount, or even splits in two. Such a differential measurement would serve to offset drifts in the lattice constant due to uninteresting variations in the environment such as temperature fluctuations or varying humidity. In other embodiments consistent with the present invention, stacked identical domains with different functionalization could be used to distinguish between closely related stimuli, one of which affects the upper domain more strongly and the other of which affects the lower domain more strongly.

In other embodiments consistent with the present invention, many of the same benefits can be attained also by placing non-functionalized and differentially functionalized domains in two-dimensional or even one-dimensional arrangements. The ultimate limit of this would be a graded crystals sensor whose functionalization and lattice constant changes continuously through its length, area or volume.

Sensor arrays can be used to detect ambient stimuli directly through their influence on particle-bound ligands. In other embodiments consistent with the present invention, sensor arrays also can be used in two- or multiple stage detection techniques.

Figure 11A:
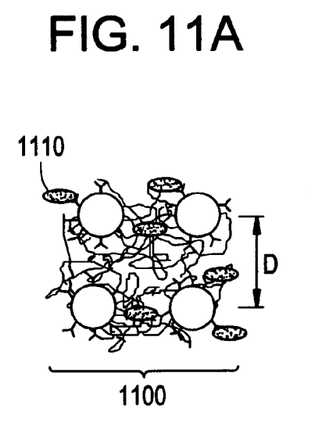
FIGS. 11A-11C are schematic representations of a gelled sensor array used in two- or multiple stage detection techniques.
Figure 11B:
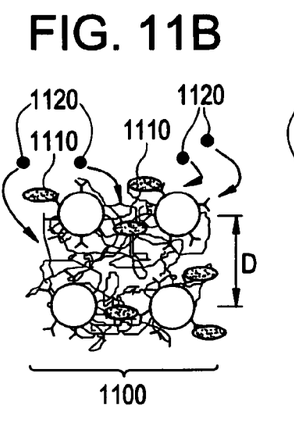
Figure 11C:
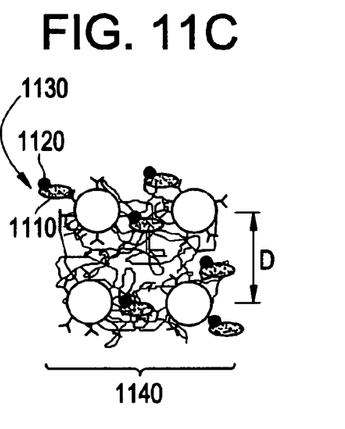

For example, consider FIG. 11A in which a gelled sensor array 1100 binds a stimulus 1110 which has no immediate effect on the array's lattice constant D. Subsequent treatment with another physical or chemical process, represented schematically in FIG. 11B by 1120, converts the bound stimulus into a new entity 1130, as shown in FIG. 11C, which now influences the array's lattice constant, leading to a detection. The transformation induced by process 1120 might involve binding an antibody to a previously bound protein stimulus; selective chemical oxidation or reduction of the bound stimulus; or an optically induced transformation, in which case entity 1130 should be understood to represent the action of light on the bound target 1110. Other possible transformations of bound stimuli might include thermal processing.

This approach offers several benefits over conventional methods for detecting proteins, carbohydrates, and related biologically derived materials in mixed samples. These benefits include the ability to use selective binding sites on easily prepared colloidal particles to detect each of the targeted molecules. These binding sites' selectivity can be chosen to optimize sensitivity and discrimination of similar targets without concern for optimizing synthesis conditions for each type of binding molecule simultaneously. The resulting sensor array 1140 of FIG. 11C can be exposed to an unknown sample in any of a number of ways, including dipping and surface contact on solid samples. The array 1140 then can be rinsed and activated with simple chemistry capable of detecting only the presence and not the identity of the bound molecules. Detecting the presence of bound proteins, for example, could be accomplished by treating an exposed array to protease and ATP in solution. Any domains which have bound target proteins will swell as the bound proteins are metabolized and their presence detected through a change in the diffracted wavelength of their crystalline domain.

Thus, differences in particle composition, size, and coatings on the spheres, in addition to their separation and symmetry, as well as their chemical functionalization, affect their response to target stimuli.

Consequently, the gelled sensor arrays 1140 described above should have applications as gene chips, protein chips, carbohydrate chips, and other applications where rapid detection and discrimination of large numbers of closely related molecules are required. This would have immediate applications in testing food, pharmaceuticals, cosmetics and other products whose freedom from pathogens must be assessed frequently and economically. The gelled sensor system could be dipped into samples of the product under testing for immediate measurements of such characteristics as heavy metal contamination, salt concentration, and pH. It can be subsequently or alternatively processed through a multistep detection method to seek out pathogens or their metabolites. More general multistep detection schemes can be designed along the same principles for these and other applications.

Figure 12:
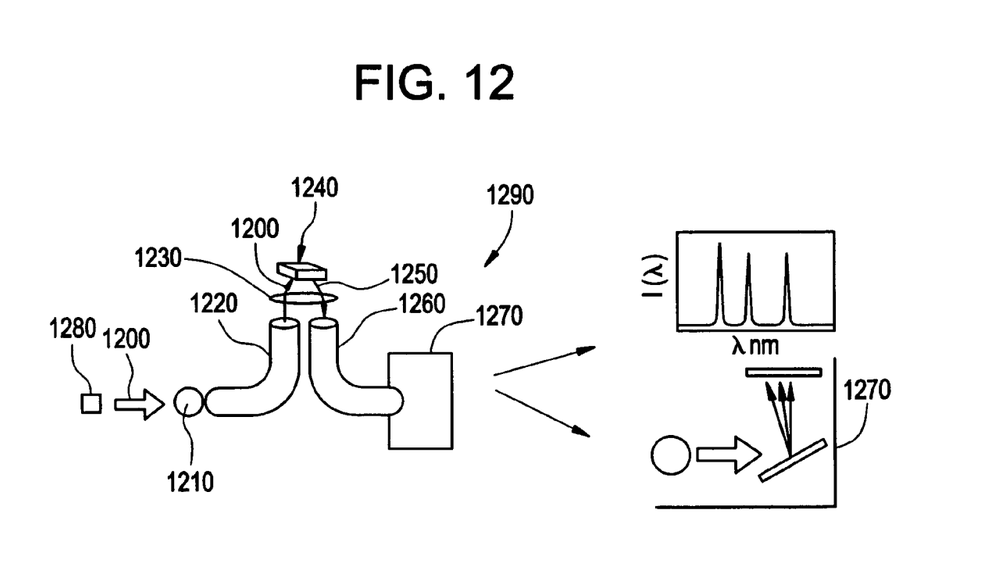
FIG. 12 is a schematic representation of a gelled sensor array placed at the end of an optical fiber for optical readout with a fiber spectrometer, to form an integrated all-optical sensor system, according to one embodiment consistent with the present invention.

Gelled sensor arrays could be placed at the end of the optical fibers for optical readout with a fiber spectrometer, to form an integrated all-optical sensor system 1290 as shown in FIG. 12. The gelled sensor array can monitor shifts in the domains' characteristic diffraction peaks. For example, two-layer domains consisting of fifty or so colloidal spheres yield easily measured diffraction signatures. Several hundred distinct domains therefore, could be integrated into the optical detection system of FIG. 12.

As shown in FIG. 12, white light 1200 from a light source 1280 is launched with coupling optics 1210 into a multi-mode optical fiber 1220. This fiber 1220 projects the white light 1200 through beam-shaping optics 1230 onto the back side of a gelled sensor array 1240. This array 1240 diffracts light into all directions. Only limited directions are collected by the beam-shaping optics 1230 and the return optical fiber 1260. Because each of the sensor domains in the array 1240 is designed only to diffract particular wavelengths into this acceptance angle, the returned light 1250 will contain only those specific wavelengths. This light is transferred by fiber or fiber bundle 1260 to a spectrometer 1270 capable of resolving these diffracted wavelengths and reporting the result either to the end user, or else to an automated read-out system. The entire system 1290 composed of light source 1280, projection optics 1210, collection optics 1230, and spectrometer 1270 constitutes an integrated all-optical sensor system 1290.

The spectrometer 1270 might be selected from the class of highly portable hand-held fiber spectrometers. Analyzing the diffraction pattern for variations in individual lines' wavelengths and thus, for variations in exposure to environmental stimuli requires minimal computational effort and could be handed with a simple embedded processor, or by interfacing to a handheld computational device. In this case, the entire system 1290 could be integrated into a hand-held broad spectrum sensor system. Such a sensor system could be integrated easily into a more general portable information processing system. Such information processing systems include handheld computing capability, wireless communications and global positioning reception. The integrated optical detection system described herein can be integrated easily into such a system. This integrated system then can report its position and detection status to a central data analysis station.

Figure 13:
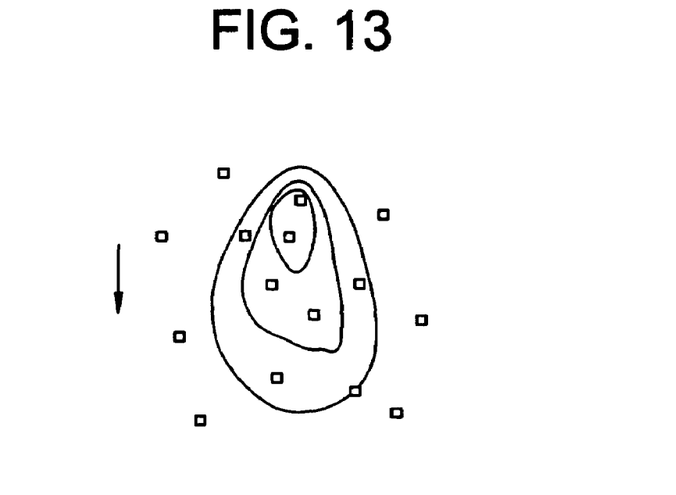
FIG. 13 is a schematic representation of deployment of multiple examples of a portable sensor system, according to one embodiment consistent with the present invention, which can interoperate with others deployed in an area to provide an overall view of environmental conditions and their evolution over time.

The presence of many detectors simultaneously testing for a wide range of environmental threats and reporting their results and positions makes possible quantitative assessment of the nature, extent and duration of any detected anomaly. Each portable sensor system therefore, can interoperate with others deployed in an area to provide an overall view of environmental conditions and their evolution over time. FIG. 13 offers a simplified view of such interoperation in the field, where multiple reporting units deployed in the field provide a quantitative distributed view of the spread of an environmental contamination event. This would have widespread applications both in battlefield command and control as well as in environmental testing for industrial process control and contamination detection and remediation.

The gelled sensor arrays 1240, as they are highly customizable, can have many applications. For example, sensor crystals can be packed with food, pharmaceutical and other products during shipping to detect byproducts of degradation and adulteration. The gelled sensor arrays can sense the products to detect byproducts etc., and then can be inspected at a later time by a simple pass through a scanning system to assess a wide variety of possible in-shipment changes. Thus, reading of the response of the gelled sensory arrays do not have to be made in real-time.

Such applications as described above, might be extended to safeguarding consumer products, and for monitoring the stability of materials for long-term storage.

A single gelled sensor can also simultaneously monitor a range of different stimuli, ranging from airborne chemical and biological agents to doses of ionizing radiation.

The sensor elements may be disposable, and may be easily replaced when contaminated or to select different tests.

The reader maybe any suitable commercially provided handheld device and can be configured to transmit data to central locations via wireless links. The device also may display simultaneous real-time analyses of all tests for the operator as well.

The optical signals from the device are by their nature not susceptible to contamination or interference. The equipment is thus well suited to hazardous environments and to remote deployment and operation as by being dropped out of aircraft.

In another embodiment consistent with the present invention, the gelled sensors can be provided in a bundle or "brush" 1300 (see FIG. 14), and an operator may examine a large area by sweeping the sensor bundle or brush 1300 over the targeted area. The brush arrangement provides contact of the sensing element with targets in situ as opposed to having to transfer a sample to a chip.

Figure 14:
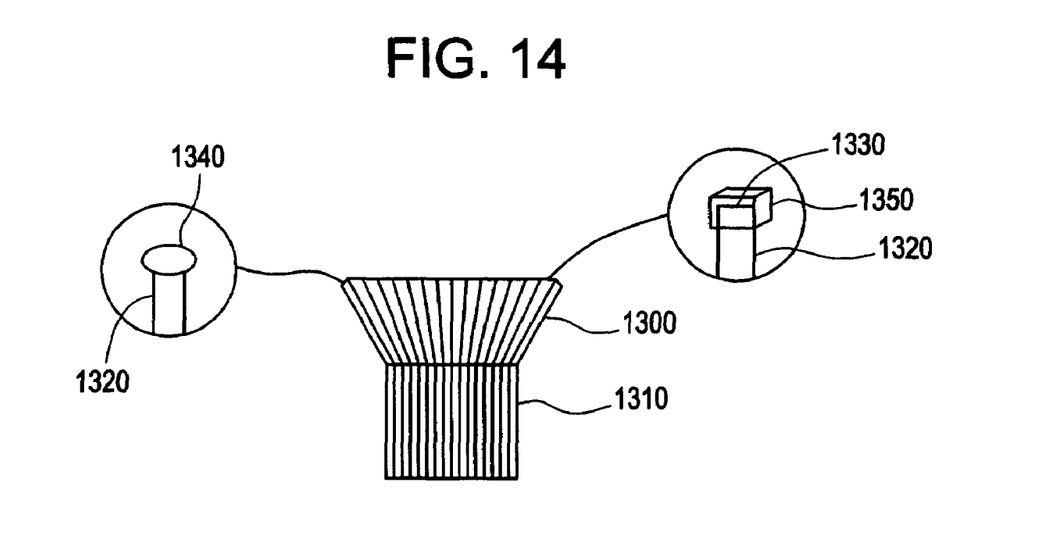
FIG. 14 is a schematic representation of a brush approach according to one embodiment consistent with the present invention, for use in sensing and detecting biological, chemical and radiological threats in a wide variety of types of samples.

Each fiber 1320 in the brush 1300 is a sensor element which can be swept across surfaces or in an air or water flow. The fibers or bristles of the brush would preferably be free and the fibers flexible. With the use of a brush approach, the sensor is not limited to surfaces, and they can be inserted into crevices and places where it would normally be difficult to obtain readings.

Further, instead of gelled sensor arrays, beads 1340 (also shown in FIG. 14), which are responsive to a particular target stimulus, can be disposed, and can be arrayed, at the end of each fiber 1320 of the brush 1300, to provide the response to the target stimulus.

A sleeve 1310 (see FIG. 14) can be provided around the brush 1300 such that the sleeve 1310 can provide a sufficiently rigid structure to insert the sensors into a loosely packed material, for example. The sleeve 1310 can be formed of any material which would be sufficiently rigid, such as plastic or metal. Once inserted, the sleeve 1310 can be retracted such that the gelled sensor arrays 1330 can sense the material, react to the stimulus, and the response can be read.

Different sensors that are responsive to different stimuli can be provided on the various fibers or bristles 1320 of the brush 1300 (i.e., tests on separate fibers). Further, tests for the same target stimulus can be distributed on the bristles at different sensitivity levels to semi-quantitate or verify quantitation, as well as provide a basis for statistics and greatly reduce false positives and false negatives.

Further, a hardened permeable screen 1350 of metal or nylon, or other suitable material, can be provided on the tip of each fiber 3120 of the brush 1300 (i.e., a sensor pad) such that the gel of the sensor array 1330 is not abraded during use (see FIG. 14).

Teams of operators may use the brushes to sweep assigned portions of a contaminated area. Results are reported simultaneously, or can be read later, and correlated in the field to develop pattern and intensity analyses.

In another embodiment consistent with the present invention, the groups appended to the colloidal particles can be designed to respond to a selected stimuli by for example, undergoing an exothermic reaction which can be detected by various means. Other biological, chemical or radiological changes to the gel can be detected to determine the target stimulus' presence. Note that the gel must be permeable to what target stimulus is being detected.

In another embodiment consistent with the present invention, when the sensor crystals are assembled with holographic optical tweezers, and the particles or spheres are in embedded in the gel and in close contact with one another, the spheres can be exposed to a stimulus such as an antigen, or strands of DNA, or a carbohydrate, etc., for example, and then certain antibodies can be bound to the spheres. In particular, different spheres of different sizes which react to a number of different antibodies, can be used.

Thus, the spheres selectively bind to certain antibodies, and can bridge small gaps between the spheres. The spheres therefore, become bound together, but not in the domains where the spheres do not bind with the antibodies.

If the temperature or some other chemical reaction is instituted, the gel can swell in those domains where the antibodies are bound, but do not swell in the domains where the antibodies are not bound to the spheres. Accordingly, with a change in temperature, for example, the gel will swell and the spheres will move apart, and the diffractive wavelength will shift to the red. Thus, this change in color can be measured by a spectrometer.

In another embodiment consistent with the present invention, as one of ordinary skill in the art would be aware, the present invention can be used in nucleic acid hybridization. In particular, a binding agent can be used to bind two items together by a third entity, such as by using a hybridization DNA assay, leptins, carbohydrates, or biotin etc. In nucleic acid hybridization, there would be a specific code provided with the nucleic acid, which would look for a specific sequence. Thus, for example, beads could be coated with probes having a sequence coated with one or more nucleic acid probes having a sequence from more than one region to target a particular nucleic acid.

In addition, materials can be included to process the target and make it more accessible for the probe and the reactive substance on the bead. For example, nucleic acid hybridization can incorporate restriction endonucleases in the gel to cut up the target DNA into fragments that are more accessible to the beads (i.e., proteases in the case of proteins). Further, other items can be incorporated in the gel to facilitation the reaction, i.e., catalysts.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A sensor, comprising:
a plurality of colloidal particles each having a specific chemical receptor bound to a surface of each of said particles and functionalized to respond to a target stimulus, wherein said particles are assembled into an array, and
a gel in which said particles are embedded,
wherein said gel deforms in response to an action of said target stimulus with said specific chemical receptor.

2. The sensor according to claim 1, wherein each said particle is a bead.

3. The sensor according to claim 2, wherein each said array is provided on a movable tip of a plurality of flexible optical fibers.

4. The sensor according to claim 1, wherein each said particle comprises at least one member selected from the group consisting of silica, polystyrene, and titanium oxide.

5. The sensor according to claim 1, wherein each said chemical receptor responds specifically to each said target stimulus.

6. The sensor according to claim 1, wherein different populations of said particles are created by appending different chemical receptors to surfaces of said particles.

7. The sensor according to claim 6, wherein different particles from said different populations comprise an organization of separate domains.

8. The sensor according to claim 7, wherein said organization comprises separate domains in proximity and arranged as an assembly.

9. The sensor according to claim 8, wherein said assembly comprises an integrated sensor array.

10. The sensor according to claim 9, wherein said integrated sensor array includes different domains which are sensitive to different target stimuli.

11. The sensor according to claim 8, wherein said domains are stacked on one another in three dimensions.

12. The sensor according to claim 11, wherein said domains are stacked in a staggered manner.

13. The sensor according to claim 11, wherein a surface of one said domains includes functionalized particles and a surface of another of said domains includes non-functionalized particles.

14. The sensor according to claim 1, further comprising a medium in which said gel-embedded particles are disposed.

15. The sensor according to claim 14, wherein a response of said particles to said target stimulus includes one of a change in ionic strength, temperature, chemical composition, and pH in one of said gel and said medium.

16. The sensor according to claim 14, wherein said particles are made of a material having a dielectric constant which is different from that of a dielectric constant of at least one of said medium and said gel.

17. The sensor according to claim 1, wherein a lattice constant of said array changes in response to said target stimulus.

18. The sensor according to claim 17, wherein said change in said lattice constant is measured using a spectrometer.

19. The sensor according to claim 1, wherein said response to said action is a color change.

20. The sensor according to claim 1, wherein said array is at least one layer.

21. The sensor according to claim 1, wherein said gel is a hydrogel.

22. The sensor according to claim 1, wherein a diffraction pattern of said array changes in response to said target stimulus.

23. The sensor according to claim 1, wherein said array is composed one-dimensional chains of particles and two-dimensional domains of particles in a monolayer.

24. The sensor according to claim 23, further comprising one-dimensional chains which are non-functionalized and disposed between functionalized domains of particles.

25. The sensor according to claim 23, wherein said array is a multi-dimensional array including a two-dimensional array and a three-dimensional array, and wherein said one-dimensional chains, said two-dimensional domains, and said three-dimensional arrays are arranged such that said particles have a distinct spacing and a distinct diffraction signature.

26. The sensor according to claim 25, wherein each said response to said target stimulus includes a shift in wavelength of a characteristic diffraction peak of each of said different domains.

27. The sensor according to claim 1, wherein said target stimulus is one of a nucleic acid, protein, carbohydrate, and lipid.

28. The sensor according to claim 1, wherein each said array is provided on a movable tip of a plurality of flexible optical fibers.

29. The sensor according to claim 28, further comprising a sleeve which encloses said fibers.

30. The sensor according to claim 29, wherein said sleeve is retractable.

31. The sensor according to claim 28, wherein each said array on said tip of said fibers is responsive to a different target stimulus.

32. The sensor according to claim 28, wherein each said array on said tip of said fibers is responsive at a varying sensitivity level to a same target stimulus.

33. The sensor according to claim 28, further comprising a screen disposed on said tip of said fibers to protect said array.

34. The sensor according to claim 28, further comprising at least one of a plurality of products disposed in said array.

35. The sensor according to claim 1, wherein said target stimulus causes aggregation of the plurality of particles.

36. The sensor according to claim 35, wherein said target stimulus comprises an antigen.

37. The sensor according to claim 35, wherein said response to said target stimulus is one of a chemical, biological, and radiological change.

38. A sensor, comprising:
a plurality of colloidal particles each having a specific chemical receptor bound to a surface of each of said particles and functionalized to respond to a target stimulus, wherein said particles are assembled into an array, wherein a lattice constant of said array changes in response to said target stimulus.

39. The sensor according to claim 38, wherein each said particle is a bead.

40. The sensor according to claim 39, wherein each said array is provided on a movable tip of a plurality of flexible optical fibers.

41. The sensor according to claim 38, wherein each said particle comprises at least one member selected from the group consisting of silica, polystyrene, and titanium oxide.

42. The sensor according to claim 38, wherein each said chemical receptor responds specifically to each said target stimulus.

43. The sensor according to claim 38, further comprising at least two specific chemical receptors bound to a surface of each of said particles and functionalized to respond to different target stimuli.

44. The sensor according to claim 43, wherein different particles from said different populations comprise an organization of separate domains.

45. The sensor according to claim 44, wherein said organization comprises separate domains in proximity and arranged as an assembly.

46. The sensor according to claim 45, wherein said assembly comprises an integrated sensor array.

47. The sensor according to claim 46, wherein said integrated sensor array includes different domains which are sensitive to different target stimuli.

48. The sensor according to claim 45, wherein said domains are stacked on one another in three dimensions.

49. The sensor according to claim 48, wherein said domains are stacked in a staggered manner.

50. The sensor according to claim 48, wherein a surface of one of said domains includes functionalized particles and a surface of another of said domains includes non-functionalized particles.

51. The sensor according to claim 38, further comprising a gel in which said particles are embedded.

52. The sensor according to claim 51, further comprising a medium in which said gel-embedded particles are disposed.

53. The sensor according to claim 52, wherein a response of said particles to said target stimulus includes one of a change in ionic strength, temperature, chemical composition, and pH in one of said gel and said medium.

54. The sensor according to claim 52, wherein said particles comprise a material having a dielectric constant which is different from that of a dielectric constant of at least one of said medium and said gel.

55. The sensor according to claim 51, wherein said gel deforms in response to an action of said target stimulus with said specific chemical receptor.

56. The sensor according to claim 51, wherein said gel is a hydrogel.

57. The sensor according to claim 38, wherein said array is at least one layer.

58. The sensor according to claim 38, wherein said array is composed one-dimensional chains of particles and two-dimensional domains of particles in a monolayer.

59. The sensor according to claim 58, further comprising one-dimensional chains which are non-functionalized and disposed between functionalized domains of particles.

60. The sensor according to claim 58, wherein said array is a multi-dimensional array including a two-dimensional array and a three-dimensional array, and wherein said one-dimensional chains, said two-dimensional domains, and said three-dimensional arrays are arranged such that said particles have a distinct spacing and a distinct diffraction signature.

61. The sensor according to claim 38, wherein said target stimulus is one of a nucleic acid, protein, carbohydrate, and lipid.

62. The sensor according to claim 38, wherein each said array is provided on a movable tip of a plurality of flexible optical fibers.

63. The sensor according to claim 62, further comprising a sleeve which encloses said fibers.

64. The sensor according to claim 63, wherein said sleeve is retractable.

65. The sensor according to claim 64, further comprising a screen disposed on said tip of said fibers to protect said array.

66. The sensor according to claim 64, further comprising at least one of a plurality of products disposed in said array.

67. The sensor according to claim 64, wherein each said array on said tip of said fibers is responsive to a different target stimulus.

68. The sensor according to claim 64, wherein each said array on said tip of said fibers is responsive at a varying sensitivity level to a same target stimulus.

69. The sensor according to claim 38, wherein said target stimulus causes aggregation of the plurality of particles.

70. The sensor according to claim 69, wherein said target stimulus comprises an antigen.

71. The sensor according to claim 69, wherein said response to said target stimulus is one of a chemical, biological, and radiological change.

* * * * *